United States Patent [19]

Levine et al.

[11] Patent Number: 5,759,794
[45] Date of Patent: Jun. 2, 1998

[54] ASSAY OF BLOOD OR OTHER BIOLOGIC SAMPLES FOR TARGET ANALYTES

[75] Inventors: Robert A. Levine, Guilford; Stephen C. Wardlaw, Old Saybrook, both of Conn.; Rodolfo R. Rodriguez, Owings Mills, Md.

[73] Assignee: Becton Dickins & Co., Franklin Lakes, N.J.

[21] Appl. No.: 771,506

[22] Filed: Dec. 23, 1996

Related U.S. Application Data

[60] Division of Ser. No. 247,336, May 23, 1994, Pat. No. 5,635,362, which is a continuation-in-part of Ser. No. 969,379, Oct. 30, 1992, Pat. No. 5,342,790.

[51] Int. Cl.⁶ .................. G01N 33/543; G01N 33/558
[52] U.S. Cl. .................. 435/7.24; 422/57; 422/58; 422/72; 422/101; 435/287.1; 435/287.2; 435/288.1; 435/810; 436/164; 436/165; 436/514; 436/518; 436/536; 436/541; 436/805; 436/810; 436/824
[58] Field of Search .................. 422/55, 57, 58, 422/72, 101; 435/7.24, 287.1, 287.2, 288.1, 810; 436/514, 518, 536, 541, 164, 165, 805, 810, 824

[56] References Cited

U.S. PATENT DOCUMENTS 4,197,287 4/1980 Piasio et al. .................. 422/71
5,342,790 8/1994 Levine et al. .................. 436/523

*Primary Examiner*—Christopher L. Chin
*Attorney, Agent, or Firm*—Williams W. Jones

[57] ABSTRACT

A patient's health may be diagnosed by centrifuging blood samples in a transparent tube, which tube contains one or more bodies or groups of bodies such as floats, inserts, liposomes, or plastic beads of different densities. Each density-defined body carries analyte-capture binding materials such as antigens or antibodies, which are specific to an epitope, or other specific high affinity binding site on a target analyte which target analyte may be in the blood or other sample being tested; and the level of which analyte is indicative of the patient's health. At least one labeled binding material which is also specific to an epitope, or other specific high affinity binding site on the target analyte is added to the sample so as to form labeled binding material/analyte/body complexes in the sample. Upon centrifugation, the complexes will settle out in different areas in the tube according to the respective density of the body or bodies; and the degree of label emission of the complex layers can enable qualitative and/or quantitative analyses of the sample to be made. Unbound labeled binding materials will be separated from the complexed layers by the washing action of ascending or descending components of the sample during the centrifugation step. Unbound labeled binding material will thus not interfere with the analysis.

3 Claims, 1 Drawing Sheet

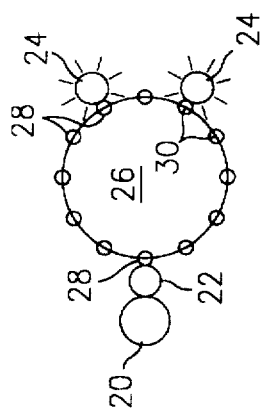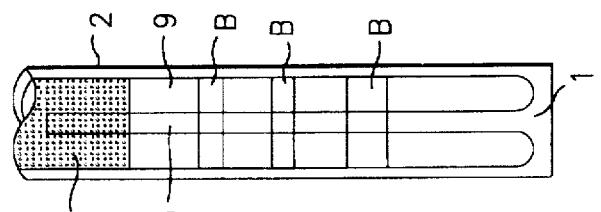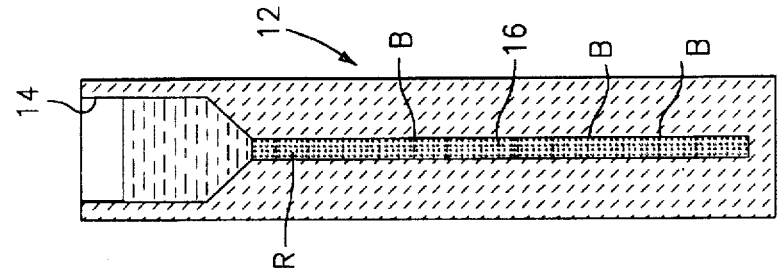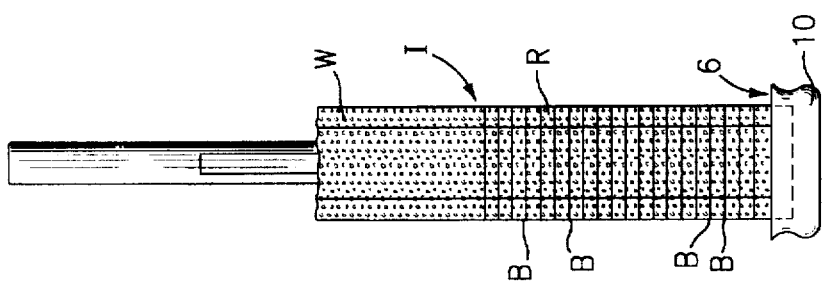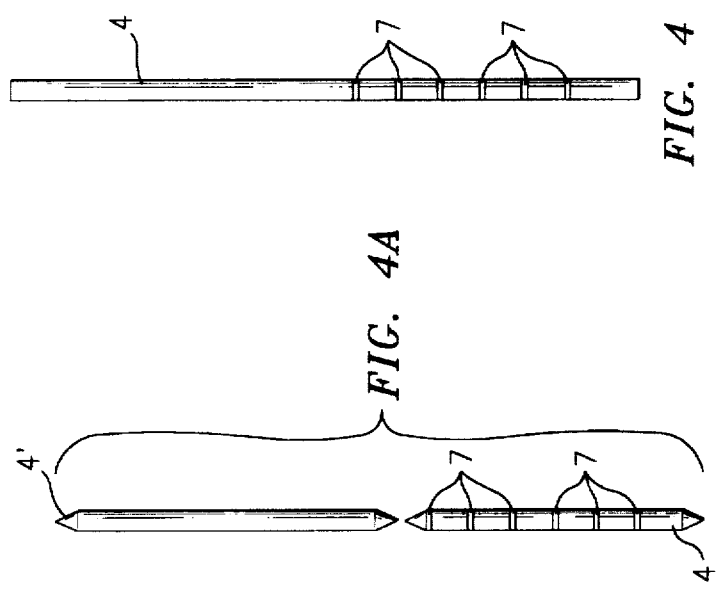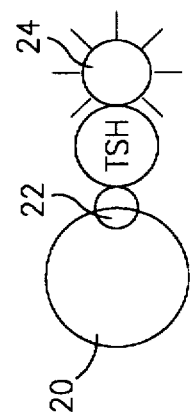

ASSAY OF BLOOD OR OTHER BIOLOGIC SAMPLES FOR TARGET ANALYTES

This is a division of U.S. Ser. No. 08/247,336, filed May 23, 1994, now U.S. Pat. No. 5,635,362 which in turn is a continuation-in-part of U.S. Ser. No. 07/069,379 filed Oct. 30, 1992, now U.S. Pat. No. 5,342,790.

TECHNICAL FIELD

This invention relates to the one-step simultaneous determination of the presence or absence of a target analyte or analytes, and where desired, analyte quantification in a whole blood, anticoagulated whole blood, blood plasma, blood serum, saliva, cerebrospinal fluid, lymph, urine, or other biological fluid sample. More particularly, this invention involves the use of target analyte-capture bodies which are caused to settle into a predetermined location in a transparent tube, and also involves labeling of the captured analyte.

BACKGROUND ART

Analyses of blood samples for the presence or absence of antibodies or antigens are used in the diagnosis of diseases, such as HIV infection, hepatitis, Lyme disease, prenatal profiles including TORCH (an acronym for: "Toxoplasmosis, Rubella, Cytomegalovirus, Herpes") profiles, as well as other infectious disease profiles. Presently, such serologic diagnoses are often performed by fluorescent immunoassay. Immunofluorescent assays are not only used for detection of antigens and antibodies in infectious diseases but are widely used for detection of autoimmune phenomena and for localizing pathologically altered serum or tissue elements, e.g., Graves disease, connective tissue diseases, multiple sclerosis, kidney disease, myasthenia gravis, pemphigus, pemphigoid, as well as many pathologic conditions such as cirrhosis of the liver, vasculitis etc. Analyses may also be performed to measure the levels of hormones such as insulin, thyroxine, thyroid stimulating hormone (TSH), blood coagulation factors, factor VIII, von Willebrand factor; and levels of other possible blood constituents, such as digoxin, morphine, and also blood vitamins such as $B_{12}$ and folic acid; as well as any other substances which may be present in small amounts in the biologic sample, which substances have a specific binder available.

Non-immunologic binding pairs include systems wherein the two components share a natural affinity for each other but are not antibodies. Exemplary non-immunologic pairs are biotin/streptavidin or biotin/avidin; intrinsic factor/ vitamin $B_{12}$; folic acid/folate binding protein; hormone/ thormone receptor; nucleic acid complexes; antibody/ antibody binding protein, i.e., IgG/protein A; DNA/DNA; DNA/RNA/; carbohydrates/lectins; complementary peptide sequences; complementary nucleotide sequences; effector/ receptor molecules; enzyme cofactors/enzymes; enzyme inhibitors/enzymes; a peptide sequence/antibodies specific for that sequence protein; polymeric acids/bases; dyes/ protein binders; peptides/specific protein binders; and the like.

In a standard indirect fluorescent immunoassay, an antigen, which is the coupling partner for the antibody to be detected, i.e. float tissue culture cells for DNA antigen, or tissue (skin, liver, muscle, etc) or any microorganism or virus, is first affixed to a solid support medium such as a glass slide. With soluble antigens, a paper membrane, nitrocellulose or nylon membrane (Dot blot Technique) can be used. A sample of serum from the patient is then allowed to incubate in contact with the affixed antigen for a period of time sufficient for the partner antibody, if present, to become attached to the affixed antigen. The support surface is then washed to remove all unbound antibodies. A reagent consisting of a labelled antibody to human immune (antibody) globulins is next brought into contact with the support surface and incubated for a time sufficient to cause linkage of the labeled material and any traces of the patient's antibodies which may have bound to the fixed antigen. The excess reagent is then washed off and the support surface is examined to determine if any label is present. Examination of the prepared sample, depending upon the nature of the label, can be done visually; or by spectrophotometry or fluorometry; or by radiation detection means.

It will be appreciated that the aforesaid procedure requires multiple specimen handling steps, including washing, and analysis techniques, and is thus labor intensive and time-consuming. The aforesaid procedure is usually used to detect the presence or absence of only one antigen-specific antibody per test but under certain circumstances two different fluorescent dye labels (fluorescein and rhodamine) are used if one suspects that at least two antibodies may be implicated and characteristic in the suspected disease, i.e., basement membrane antibody as well as DNA antibody, and the substrate used is, for example, a skin section. Usually an antiglobulin is used as the second antibody, however if it is desired to ascertain if the antibody present in the body fluid is IgG or IgM, this can be done using specific anti-IgG or IgM or for that matter any anti-immunoglobulin. Specific immunoglobulins are often used to determine placental transfer of disease, such as syphilis, viral infections, etc, in order to ascertain if the disease is in early or late phases, or to determine whether a patient is producing a specific immunoglobulin to an antigenic stimulus. Fluorescent immunoassays for hormones, drugs and proteins of diagnostic importance have also been developed.

DISCLOSURE OF THE INVENTION

Red cells, when centrifuged in a tube containing a whole blood sample will form a continual density gradient layer in the bottom of the tube, with the most dense red cells settling on the bottom of the red cell layer. When an anticoagulated whole blood sample is centrifuged in a tube containing bodies of different specific gravity, such as cylindrical floats, beads, discs, or different specific gravity liposomes, these bodies will form spaced, distinctly visible markers in the packed red cell layer. In certain cases, the centrifuge tube may also contain a cylindrical plastic float or insert which may be fixed to the bottom of the tube or may be freely movable in the tube, and which, if freely movable, has a specific gravity such that it will preferably sink through the red cell layer in the centrifuged blood sample, or come to rest in an area where the particles also come to rest. The insert restricts the available space in the tube which the red cells, plasma, serum, or liquid phase can occupy, and therefore increases the distance between the marker rings which form in the centrifuged red cell, plasma, serum, or liquid phase layer, and displaces the beads or liposomes to the periphery of the tube where they may be seen and easily detected without their signal being extinguished by the red cells or serum. Specimens such as plasma or serum can also be analyzed for the presence of target analytes by using analyte-capturing float/inserts or microparticles of one or more characteristic densities coupled with capture binding material, so that bands of the captured analytes coupled with labeled binding material will settle into a restricted space on or between the float/insert or post in the tube, where the captured analyte bands can be observed and measured.

In one embodiment of the invention, the insert itself can be coated with the capture material, and can be centrifuged back and forth through the tube several times so that the cellular and other components of the sample are forced to pass between the insert and the tube bore wall several times. Due to the severely restricted space available for passage of the sample components between the insert and the tube, which space may be in the range of twenty to several hundred microns, and will typically be in the range of thirty five to forty five microns, the efficiency and dynamics of target analyte capture by the insert are significantly enhanced in certain cases.

In performing the method of this invention, density markers such as, for example, beads, discs, a float/insert (or float/inserts), or liposomes, will be coupled with a capture binding material such as antigens, antibodies, nucleotides, or other active binding substances whose complement, or binding partners, (which are designated herein as "target analytes") may be present in the patient's blood or other biologic sample. Examples of biologically active complementary couples include: enzymes and their substrates; nucleotides and their complementary nucleotides; aptamers (nucleotides which bind to a target analyte molecule) and their complementary molecules; naturally occurring protein binders, such as thyroid binding globulin (TBG) and thyroxine; the "intrinsic factor", and vitamin B-12; CD-4 antibody, or other specific binding substance affinity binding site and CD-4 positive cells and/or any antibody, or other specific binding substance or cells having epitope, or any specific high affinity binding sites, bound by that antibody, or other specific binding substance; and specific antibodies which will selectively couple with RNA-DNA hybrids, as described by Stollar and Rashtchian, in their article "Immunochemical Approaches to Gene Probe Assays", *Analytical Biochemistry* 1987; 161, 387–394.

Each density-marker body, or group of bodies, of which there may be one or more, will be coupled with a capture binding material, which is specific to a target analyte, which analyte may be present in the blood or other biological specimen sample. The sample is added to the tube so as to allow the density-marker/binding material capture body or bodies to incubate and intermix with the sample sufficiently to cause any target analytes present in the sample to couple with and be captured by their complementary partners on the density-markers. In certain cases, the sample-capture body-label incubation may take place during the centrifugation procedure, particularly when the latter involves reverse centrifugation of the insert back and forth through the tube. Thus the incubation step may actually take place in the centrifuge tube. One or more labeled antibodies, or other binding material moieties which may be specific to the same or to a different epitope, or any specific high affinity binding site on the target analyte, may be used to bind to, and thus label, all density-markers which have a target analyte bonded thereto.

The label may be a liposome encapsulated colorant, or a fluorescent colorant; or may be a radioactive energy emitter. The label must be detectable and preferably quantifiable. After an appropriate incubation period, the sample is centrifuged to densimetrically separate the density-markers into spaced-apart bands or rings in the tube. The different density-marker bands are then examined in the tube to determine which bands, if any, have a detectable quantity of label, and to measure the quantity of the label, if appropriate. Quantification and detection of false positive tests could be furthered by carrying out suitable control tests. The label most likely to be used would be a fluorescent molecule such as FITC (fluorescein isothiocyanate).

The types of label markers (or labels) which are employed with immunodiagnostic assays can be varied and can include labels which are observed directly, such as fluorescein; or observed after a further step, such as enzymes. Any suitable label may be employed. Examples include: enzyme labels such as alkaline phosphatases; peroxidases; acid phosphatases; chemiluminescent materials; bioluminescent materials; fluorescent labels; and electron dense labels. Typically, the label is a protein. The labels may be attached to the target analyte by any suitable technique.

If desired, the different density beads can have different intrinsic colors, so that each (if there are more than one band) differently colored band will designate a different target analyte. If differently colored labeled binding material moieties are used, the colors of the labeled bands in the tube will indicate which bound analytes are in the sample, and which analytes are not, in the event that bands of density-markers placed in the tube do not demonstrate any label associated therewith. This information, of course, permits diagnosis of the health of the sample donor in regard to the parameters being evaluated. The assay will provide the physician with a valuable adjunct to conventional diagnostic tests and will permit the rapid acquisition of diagnostic data and the rapid screening and identification of elements sought after in the sample.

In accordance with one embodiment of the invention, a fluorescent assay of a whole blood or blood product sample can be made in a tube and float/insert paraphernalia sold by Becton Dickinson and Company under the trademark QBC®. The labelled binding particle is a particle which is specific against the same or a second epitope, or any specific high affinity binding site on the target analyte. The density marker particles may be differentially colored, one density from another, and the labelled binding particles may also be differentially colored, one from another.

In cases where it is desired to perform one or more simultaneous assays in the same QBC® tube, the labeled binding materials' tag or label may be identical, since the labeled binding material will be detected by either its position in the tube, which will be a function of the density of the particle or float/insert to which it is attached, or the position of the labeled binding material on the float/insert, if the capture binding material is coated circumferentially around a float/insert in a band or bands, with multiple capture binding material bands being positioned on the float, which bands are separated by discernible distances on the float/insert. As previously noted, the labeled binding materials may alternatively be provided with different detectable labels. By measuring the amount of each label, one can quantify the amount of target analyte present in the sample, since the intensity of the label signal will be proportional to the amount of labeled analyte in the specimen sample.

A variety of immunodiagnostic assays are known to persons of ordinary skill in the art and can be adapted for use with this invention. For example, a target analyte can be detected in accordance with the present invention in a competitive assay. In a competitive assay, a labeled marker competes with unknown sample analyte for a limited number of complementary specific binding pair member sites immobilized on a solid phase support, such as a sphere, liposome, float/insert, or the like. The detectable marker that is bound and quit is thers inversely proportional to the unknown analyte.

It is therefore an object of this invention to provide an improved technique for analyzing a biological specimen sample to determine the presence or absence of certain target analytes therein.

It is a further object to provide an improved technique of the character described wherein the analysis is performed densimetrically in a transparent specimen tube.

It is an additional object of this invention to provide an improved technique of the character described wherein the analysis is performed by using spatially resolvable markers which may have different specific gravities, and which are coupled to capture materials such as antibodies and/or antigens so that one or more of different multiple assays may be performed in one tube at the same time.

It is another object of this invention to provide an improved technique of the character described wherein the analysis is performed by forming, for example, highlighted antibody/antigen couple bands in the sample.

Still a further object of the invention is the elimination of many of the tedious procedural steps such as washing, agitation, preparation of numerous reagents such as buffers, blockers and absorbents etc. which are needed to perform numerous titrations of reagents necessary in prior art assay procedures.

Another object is the elimination of time-consuming procedures such as lengthy incubation steps, as for example are necessary in the ELISA assay often used in similar applications.

Another object of this procedure is the decreased use of radioisotopes and the special apparatus necessary for handling such samples and reagents.

This invention allows for the determination and/or quantitation of very small amounts of analyte, using very small amounts of biologic sample and reagents. A number of important advantages of this procedure are that this assay can help establish if a disease pathology is the result of an allergic mechanism, e.g. rheumatoid or connective tissue diseases; establish the specific organism responsible for a disease; establish the course of a disease by following antibody, or other specific binding substance titres, which this test can readily do; determine whether an infant has been infected in utero; and the like.

These and other objects and advantages will become more readily apparent from the following detailed description of a preferred embodiment of the invention when taken in conjunction with the accompanying drawings in which:

DESCRIPTION OF THE DRAWING

FIG. 1 is side elevational view of a centrifuge tube adapted to perform the procedure of this invention;

FIG. 2 is a view of the tube of FIG. 1 showing a centrifuged whole blood sample therein, and with the red blood cell layer being blown up or increased in size to particularly point out the nature of the invention;

FIG. 3 is an axial sectional view of a second embodiment of a centrifuge tube adapted for use in performing the invention;

FIG. 4 is a side elevational view of a float/insert with a number of spaced-apart antibody, or other specific binding substance bands coated thereon, along the axial length thereof;

FIG. 4A is a view similar to FIG. 4, but showing an embodiment using two float/inserts, one for analyte analysis, and the other for a second analyte or for other purposes;

FIG. 5 is a schematic representation of the invention in use to detect the analyte TSH (thyroid stimulating hormone) in a blood sample;

FIG. 6 is a fragmented side elevational view of an embodiment of the invention which can be used with a centrifuged sample of the type described above, or with a sample which displaces the target analyte in a blood sample below the red cells in a centrifuged blood sample; and FIG. 7 is a schematic representation similar to FIG. 5, but showing how the invention can be used to detect analyte cells in a fluid sample.

DETAILED DESCRIPTION OF THE INVENTION

Referring now to FIGS. 1 and 2, there is shown in FIG. 1 a tube 2, which may be a glass capillary tube, or other transparent tube, and which may contain a float/insert 4 made of a plastic, which has a specific gravity that causes the insert 4 to settle through the red blood cells to the bottom 6, or elsewhere depending on the specific gravity of the float, in the tube 2 when the latter is centrifuged with an anticoagulated whole blood sample therein. The fraternal groups of capture material-coupled plastic beads or liposomes of different specific gravities or densities may be disposed in a clump 5 in the tube 2. A plastic cap 10 closes the bottom 6 of the tube 2. The specific gravity of each group of beads will be greater than the specific gravity of the lightest of the red cells, ie, the youngest reticulocytes.

The blood sample is drawn into the tube 2 and, after a suitable incubation period, is centrifuged therein along with the insert 4 and beads 5. The bead clump 5 disperses in the blood sample during the incubation period, and then settles into distinct bands which form lines in the red cell layer as shown in FIG. 2 during the centrifugation step, while the float/insert 4 settles into and through the red cells R. The tube 2 will also contain the tagged or labeled analyte-specific binding material described above.

The white cells W layer out in bands above a red cell/ white cell interface 1. The density-marker bead bands B layer out densimetrically in the red cell layer. Examination of the bands B will indicate which of the bands B have been labeled since the fluorophore labels will be detectable only in labeled bands.

FIG. 3 shows an alternative form of centrifuge tube which can be used to practice the invention. The tube 12 has a compound funnel-shaped bore with an enlarged open end part 14 and a restricted closed end part 16. It will be appreciated that the tube 12 could also have an end closure cap as previously described, if necessary. The bore is sized so as to cause the majority of the red cells R in the centrifuged blood sample to settle into the restricted part 16 of the bore, with the majority of the plasma staying for the most part in the enlarged part 14 of the bore. The tagged density-marker bands B disperse in the centrifuged red cell layer. The tube 12 is formed from a transparent glass or plastic material. It will be noted that the embodiment shown in FIG. 3 does not use a float component.

It will be noted from FIGS. 2 and 3 that the density-marker bands are sufficiently spaced apart that each can be assayed for fluorescence, or other energy emissions, and can even be quantified as set forth hereinafter, without interference from any other bands B. When a blood sample is assayed, the nature of the red blood cells, i.e., the fact that they pack when centrifuged in a manner which excludes significant amounts of the plasma, ensures that virtually all of the non-bound labeled binding material in the tube will end up in the plasma layer, and will not interfere with the procedure.

When the sample is being analyzed for a particular nucleated cell analyte (i.e., a cell having a nucleus), the sample may have added thereto a non-specific nuclear colorant, such as a DNA-specific stain, as for example HOECHST-3542; 7 AAD; propidium iodide; SY3-8; or DAPI; or a colorant that stains both DNA and RNA such as acridine orange or thiozole orange. Any of the aforesaid colorants will stain all nuclei, including the non-analyte white cells. When the sample is centrifuged, the non-analyte nucleated cell bands will form above the red cell layer, and the captured analyte nucleated cells will, by virtue of the density of their capture particle, either settle down into the red cell layer or rise above the buffy coat to form a detectable fluorescence therein. Thus there will be two areas of fluorescence in the sample, one being the white cell or buffy coat layer, and the other being the captured nucleated cell analyte located within the red cell layer or above the white cell layer. The captured analyte cell layer can be quantified in the following manner. Assume that the target captured white cell is a particular type of lymphocyte. The lymphocyte-monocyte cell layer in the buffy coat is measured using the QBC® technique, which technique is described in U.S. Pat. No. 4,027,660. The instrument then measures the intensity of the fluorescence emanating from the lymphocyte-monocyte cell layer in the buffy coat; and then measures the intensity of the fluorescence emanating from the captured analyte cell layer within the red cell layer. The relative captured analyte cell count is then derived by proportioning the respective fluorescent intensities, and multiplying the lymphocyte-monocyte cell count by the resultant proportion decimal. This procedure is enabled by the fact that the red cells will not take up any of the acridine orange stain. The resultant relative analyte cell counts will be corrected as follows. The proportion of captured cell fluorescence viz the base line buffy coat cell fluorescence can be determined empirically, bearing in mind that the base buffy coat cell layer will be, depending on the size of the assay tubes and capture bodies used in the system, 3 to 5 cells thick, while the captured cell layer will be 1 to 2 cells thick.

Referring now to FIG. 4, a second embodiment of the invention is disclosed. In this embodiment, the float/insert 4 has one or more bands 7 of the analyte-capture binding material coated thereon at axially spaced-apart locations on the float/insert 4. Each band is clearly distinguishable from all of the other bands because of the distance between adjacent bands 7. The position of the various bands on the float/insert 4 is indicative of the type of analyte-capture material utilized. In this way the identity of any labeled analytes which bind to the bands 7 can be confirmed. For example, the lowest band on the float/insert can be a binding material specific to Lyme disease; while the next lowest band 7 can be a binding material specific to HIV; and so forth. When the binding material-banded float/insert is used in performing the specimen analysis, the tube, float/insert and sample will preferably be centrifuged a plurality of times toward opposite ends of the tube, so that the float/insert will move back and forth through the sample a number of times. In this manner, the binding material coated on the float/insert can scavenge the sample for target analytes as the sample passes back and forth through the relatively narrow annulus which exists between the float/insert and tube, thereby increasing the opportunities for target analytes to be captured on the float/insert.

FIG. 4A shows an embodiment of the invention which uses two float/inserts 4 and 4' instead of one float/insert. Both of the float/inserts may be sized so that once they are placed in the tube, they will not pass each other during the centrifugation steps in the tube. Their cylindrical surfaces will be separated by pointed ends, and when a fluorescent float or label is used on floats which centrifuge into the red cell layer of the blood sample, the pointed ends on the floats will provide a readily discernible boundary between adjacent floats because of the ability of the red cells to suppress the fluorescent signal on the pointed ends of the floats. This being the case, the entire float may be coated with fluorescent material or formed from a fluorescent plastic. In the embodiment of FIG. 4A, the float/insert 4 has the capture material 7 coated thereon; and the float/insert 4' may be devoid of capture material. Both of the float/inserts 4 and 4' may or may not be formed from a material which has a specific gravity which is greater than the specific gravity of the most dense component in the centrifuge tube, so that both float/inserts sink completely through the most dense component in the sample. In cases where the floats are desired to end up in the plasma of the centrifuged blood sample, the specific gravity of one or both of the floats will be less than the specific gravity of the lightest of the cells in the blood sample. When the assembly is centrifuged, the float/insert 4 may settle completely into the red blood cell or other density gradient layer, and the float/insert 4' may settle partially or completely into the red cell or other density gradient layer, and may, when the sample is blood, extend upwardly through the buffy coat to expand the constituent buffy coat cell layers in accordance with the prior art teachings. Both of the float/inserts can be used to capture analyte if desired. As noted previously, both floats may end up in the plasma layer of the blood sample if so desired to accommodate an expected low level label signal from captured and labeled analyte.

When two or more float/inserts are used, one of the float/inserts can be coated with the label material, as for example, with fluorescein, to a degree which will serve as a reference base which can be used to compare with the label signal intensity from the captured analyte(s). Alternatively, the reference float may be formed from a fluorescent plastic. In this way, an analyte quantitative count can be obtained. For example, if the target analyte were a cell, the coated fluorescence could be present in a degree that would represent a known count of the target cells. Comparison of the level of fluorescence from the captured analyte band would then be compared to the level of fluorescence from the reference float/insert, and the captured analyte count would then be derived by the instrument software; and the captured analyte count is displayed by the instrument.

Referring to FIG. 5, a schematic representation is shown which illustrates the manner in which the invention can be used to detect the presence of TSH (thyroid stimulating hormone) molecules in a sample of anticoagulated whole blood. The density-controlled capture particles 20 have a capture agent 22 coupled thereto which is specific to one epitope, or any specific high affinity binding site, i.e. the T epitope on the TSH analyte so as to bind the TSH analyte to the particle 20. The labeled binding agent 24 is specific to another epitope, or any specific high affinity binding site, i.e. the H epitope on the analyte, and therefore will bind to the analyte when added to the blood sample. The resultant particle-analyte-antibody, or other specific binding substance labeled complex is shown schematically in FIG. 5.

Referring now to FIG. 6, in cases where one wishes to utilize serum or plasma samples, or even with whole blood samples, when more predictable density gradients may be required, such as might be the case if many densities needed to be separated, then the lower portion of the specimen sample tube 2 shown in FIG. 6 could be prefilled with a stable material 9, such as gelled Ficoll, which has a greater density than the red blood cells, and which provides the required density gradient. This density gradient material, in addition to separating the resident bands, will serve to wash the unbound labeled binding material away from the bound layers during the centrifugation step. The tube 2 could be provided with an integral internal post 3 which projects upwardly from the bottom wall 1 of the tube 2 through the material layer 9. The specimen sample will settle onto the material layer 9, and the lowermost layer of the specimen sample, in the case of whole blood, will be the red cell layer R. Since the density marker particles 20 are more dense than the most dense component of the sample being tested, they will form spaced-apart bands B1, B2, and B3 in the material layer 9. Each band will be inspected for label presence. It will be appreciated that if a closure cap 10 such as is shown in FIGS. 1 and 2 is used, the post 3 could be formed as an integral part of the cap 10. The embodiment shown in FIG. 6 can also be used with an anticoagulated whole blood sample wherein no density gradient gel is added to the sample, and wherein the post 3 projects through the red blood cell and the white blood cell layers in the centrifuged blood sample.

A general example of the use of is invention to quantify a target analyte in a sample is as follows. The physician will identify from the literature an approximate range of how many molecules or units of a target analyte can be expected to be found in a known volume sample of the biologic fluid being assayed. For example, assume that a patient infected or exposed to Lyme Disease will be expected to have 50 Lyme analyte units per milliliter of blood at the most. The physician will add at least 100 density-marker/capture material coupled units to the blood sample per milliliter being sampled, and will also add at least 100 labeled binding material units per milliliter of sample to the container. Since there are an excess of capture sites and labeled particles in the sample as compared to the maximum number of analyte units expected to be found in the sample, the degree or intensity of label emission from the Lyme bead band will be proportional to the number of Lyme analytes which are actually present in the sample. A quantification of the Lyme analyte in the blood can thus be approximated by measuring the emission intensity. The key to the quantification procedure is to provide a functional excess of capture sites and labeled binding material units in the sample as compared to the maximum number of analyte units which can be expected to be found in the sample. One may still be able to quantitate the analyte even if the bound labeled binding material units are present in molar amounts less than the analyte, provided that there exists a mathematical relationship between the amount of analyte present and the amount of analyte eventually captured by the density marker/labeled binding material couples.

An example of a type of another target analyte that can be detected by the invention is a subset of lymphocyte blood cells. Normal human blood contains a relatively predictable amount of a subset of lymphocyte cells which have a surface epitope, or any specific high affinity binding site identified as CD4. It has been verified that the CD4 lymphocyte population in the blood of one who has been infected by HIV eventually declines, before the infected individual demonstrates symptoms of the infection. Antibodies have been identified that are specific to the CD4 epitope, or any specific high affinity binding site of these lymphocytes, and these antibodies can be attached to both the capture density marker and to the label. When cells are the analyte, rather than molecules, the epitope, or any specific high affinity binding site on the cellular analyte to which the density marker bonds can be the same or a different epitope, or any specific high affinity binding site than that the labeled binding material bonds. The reason that the cell epitope, or any specific high affinity binding site can be the same for the density marker capture substance and the labeled binding substance is because of the very large size of a cell as compared to an analyte which is generally a molecule. The principal governing this factor is illustrated in FIG. 7. Referring to FIG. 7, the cellular analyte is denoted by the numeral 26. The cell 26 will have a number of surface epitope, or any specific high affinity binding sites 28 and 30, one of which is CD4. The epitope, or any specific high affinity binding sites 28 and 30 will be specific to different binding material moieties. The numeral 20 indicates the density marker, and the numeral 22 indicates the binding material moiety bonded to the density marker 20. In the case illustrated in FIG. 7, the binding material is specific to the cell epitope, or any specific high affinity binding site 28 and will bond thereto. The surface area of the cell 26 sufficiently large, as compared to the binding material moieties 22 and 24 so as to present a very large number of available epitope, or any specific high affinity binding sites 28 and 30, so as to allow the labeled binding material moiety 24 to be specific to an epitope, or any specific high affinity binding site 30 which is different from the density marker epitope, or any specific high affinity binding site 28, or to be specific to the same epitope, or any specific high affinity binding site 28. Therefore, when a cell is the analyte, the density marker binding material and the labeled binding material may be specific to the same, or to a different, epitope, or any specific high affinity binding site on the cellular analyte. Thus the assay of CD4 lymphocytes may be accomplished with density marker/CD4 antibody couples, and labeled CD4 antibodies. Alternatively, other epitope, or any specific high affinity binding sites on the CD4 cells may be used for the density markers or for the labeled binding material moieties. Once the CD4 (or any other cellular analyte) lymphocyte/density-marker/labeled binding material complexes are formed, they can be detected and quantified in the manner described above.

Alternatively, the labeled binding material could be omitted, and a general DNA stain, such as propidium iodide could be used to quantitatively stain the cell nuclei. In such a case, the total fluorescence signal in the capture area would be directly proportional to the number of captured cells.

In the CD4 cell assay, an area of the float having not captured cells or fluorescence may be needed to provide a background count in some instances. This will take into account light scatter and fluorescence from the layer of plasma (which will contain the label such as acridine orange) that surrounds the float and lies between the float and the tube wall.

Yet another target analyte that can be detected by the invention is hematopoietic progenitor blood cells. Hematopoietic progenitor blood cells are contained within a cell population recognized with the monoclonal antibody, or other specific binding substance CD34. These cells constitute approximately 1% of human bone marrow cells, and can be found in bone marrow, peripheral blood, and cord blood. In peripheral blood of normal individuals the number of CD34 cells is approximately 0.1 to 10 per microliter (0.01% of leukocytes). This CD34 cell population number increases upon treatment with chemotherapy and/or growth factors, and numbers as high as 1,000 per microliter have been observed. In a sampling tube holding 100 µl of blood, 10 to 500 CD34 cells are thus present in normal individuals, and this number can increase to 100,000/µl in patients being treated for cancer. High dose chemotherapy has shown to be beneficial for cancer patients. Ablative chemotherapy however results in pancytopenia (a general decrease in all cell lines) which has to be rescued by reinfusion of hematopoietic stem cells. Since hematopoietic stem cells are contained within the CD34 cell population, it is essential to quantify the number of CD34 cells before they are reinfused into the patients.

Antibodies have been identified that are specific to the CD34 epitope, or any specific high affinity binding site of these blood cells, and these CD34 antibodies can be used to assay the CD34 cell population in the same general manner as described above for the CD4 cells. Once the CD34 cell/density-marker/labelled antibody, or other specific binding substance complexes are formed, they will be detected and quantified in the manner described above.

It will be appreciated that the invention has been described in connection with blood diagnosis, but the invention is also applicable to diagnose other biological fluids for the presence or absence of highly specific complementary couples found in such other biological fluids. As with the analysis of plasma, when a biological fluid other than whole blood is assayed, the centrifugation step can be performed in the density gradient fluid, such as Ficoll gel, as noted above, which will not mix with the aqueous phase of the biological fluid, and will promote densimetric separation of the bands in the density gradient fluid, with concurrent washing by the gradient fluid of the density-markers, to ensure separation of all non-bound label from the bands. This eliminates non-bound label interference with quantification of the labeled bands. The inherent washing of non-bound label from labeled cells when whole blood is being tested, and when a non-cellular fluid is being tested in gelled Ficoll, which washing occurs during the centrifugation step, eliminates the separate washing steps required by the prior art, and prevents unbound label from interfering with the accuracy of the procedure. This inherent washing is an important advantage of this invention. The labled captured analytes can be quantified by measuring the intensity of label emission eminating from the captured analyte band or bands in the sample. An instrument similar to that shown in U.S. Pat. No. 4,558,947 which is modified to include a light-intensity-quantifier can be used to perform analyte presence or absence, and/or analyte quantifications, as well as to perform buffy coat analysis.

Since many changes and variations of the disclosed embodiments of the invention may be made without departing from the inventive concept, it is not intended to limit the invention otherwise than as required by the appended claims.

What is claimed is:

1. Paraphernalia for assaying a biologic fluid sample for the presence or absence of a target analyte, said paraphernalia comprising:

a) a transparent tube for holding the sample;
   b) a completely solid cylindrical insert for placement in the tube, said insert having an external coating thereon of a binding material which is specific to a first epitope or other binding site on the target analyte; and
   c) a quantity of labeled antibodies or other binding material for placement in the tube, said labeled antibodies or other binding material being specific to a second epitope or other binding site on the target analyte.

2. The paraphernalia of claim 1 wherein said insert has a plurality of spaced-apart bands of different binding materials coated thereon, each of said bands being specific to a first epitope or other binding site on a different target analyte so as to enable said insert to scavenge different target analytes from the sample.

3. The paraphernalia of claim 2 further comprising a density gradient material in the tube into which the insert will sink upon centrifugation of the paraphernalia with a sample in the tube.

* * * * *